US008686818B2

(12) United States Patent
Dieny et al.

(10) Patent No.: US 8,686,818 B2
(45) Date of Patent: Apr. 1, 2014

(54) MAGNETIC MICROPARTICLE AND METHOD FOR MANUFACTURING SUCH A MICROPARTICLE

(75) Inventors: Bernard Dieny, Lans en Vercors (FR); Heélène Joisten, Granoble (FR); Philippe Sabon, Moirans (FR)

(73) Assignees: Commissariat a l'energie atomique et aux energies alternatives, Paris (FR); Centre National de la Recherche Scientifique, Paris (FR)

( * ) Notice: Subject to any disclaimer, the term of this patent is extended or adjusted under 35 U.S.C. 154(b) by 289 days.

(21) Appl. No.: 13/060,662

(22) PCT Filed: Sep. 17, 2010

(86) PCT No.: PCT/EP2010/063725
§ 371 (c)(1),
(2), (4) Date: Feb. 24, 2011

(87) PCT Pub. No.: WO2011/033080
PCT Pub. Date: Mar. 24, 2011

(65) Prior Publication Data
US 2011/0200434 A1 Aug. 18, 2011

(30) Foreign Application Priority Data
Sep. 17, 2009 (FR) ..................................... 09 56380

(51) Int. Cl.
*H01F 7/00* (2006.01)
*H01F 1/00* (2006.01)
(52) U.S. Cl.
USPC ............ 335/219; 335/296; 335/302; 335/306
(58) Field of Classification Search
USPC ................... 335/219, 296, 302, 306
See application file for complete search history.

(56) References Cited

U.S. PATENT DOCUMENTS 1,595,801 A * 8/1926 McDonald .................... 446/134
3,359,152 A * 12/1967 Blume, Jr. .................... 335/302

(Continued)

FOREIGN PATENT DOCUMENTS

WO WO 2009103938 A1 * 8/2009

OTHER PUBLICATIONS

Dryfus, Remi et al; "Microscopic artificial swimmers", Nature, vol. 437, Oct. 6, 2005, pp. 862-864.
S. Sudo et al.; "Magnetic Swimming Mechanism in a Viscous Liquid", Journal of Intelligent material systems and structures, vol. 17, Aug./Sep. 2006, pp. 729-736.
B.J. Nelson; "Towards Nanorobots"; Institute of Robotics and Intelligent Systems, ETH Zurich, Switzerland; Solid State Sensors, Actuators and Microsystems Conference, 2009, Transducers 2009, International IEEE, Piscataway, NJ, USA, Jun. 21, 2009, pp. 2155-2159.
Hu, Wei et al.; "High-Moment Antiferromagnetic Nanoparticles with Tunable Magnetic Properties", Advanced Materials, 2008, 20, 1479-1483, Willey-VCH, Verlag GmbH & Co.

*Primary Examiner* — Mohamad Musleh
(74) *Attorney, Agent, or Firm* — Pillsbury Winthrop Shaw Pittman LLP (57) ABSTRACT

A microparticle includes an oblong flexible tail able to propel the microparticle in a solution along a trajectory using beats transverse to the trajectory, the tail including at least one magnetic element such that the magnetic element causes beats of the tail under the action of an external alternating magnetic field non-collinear with the trajectory and a head mechanically connected to a proximal end of the tail. The microparticle includes at least one layer of material formed from one piece and including the tail and the head, the dimensions and/or shape of the head being selected such that the beats of the proximal end of the tail are limited with respect to the beats of the distal end of the tail and such that the head does not perform a complete revolution around an axis parallel to the trajectory under the effect of the external alternating magnetic field.

17 Claims, 3 Drawing Sheets

(56) References Cited

U.S. PATENT DOCUMENTS

| | | | |
|---|---|---|---|
| 3,504,316 A * | 3/1970 | Bekedam | 335/306 |
| 3,982,334 A * | 9/1976 | Tate | 434/409 |
| 7,504,921 B2 * | 3/2009 | Vranish | 335/302 |
| 7,578,788 B2 * | 8/2009 | Yokoi et al. | 600/160 |
| 7,893,801 B2 * | 2/2011 | Knobloch | 335/215 |
| 8,134,432 B2 * | 3/2012 | Knobloch | 335/215 |
| 2003/0181788 A1 * | 9/2003 | Yokoi et al. | 600/160 |
| 2007/0210886 A1 * | 9/2007 | Gerber | 335/306 |

* cited by examiner

MAGNETIC MICROPARTICLE AND METHOD FOR MANUFACTURING SUCH A MICROPARTICLE

CROSS-REFERENCE TO RELATED APPLICATIONS

This is the U.S. National Stage of PCT/EP2010/063725, filed Sep. 17, 2010, which in turn claims priority to French Patent Application No. 0956380, filed Sep. 17, 2009, the entire contents of all applications are incorporated herein by reference in their entireties.

The invention relates to a magnetic microparticle and a method for manufacturing such a microparticle. The invention also relates to a method of collective manufacturing of a plurality of microparticles according to the invention.

Microparticle is understood to refer to a manufactured particle whose dimensions are on the micrometric order. Generally, dimensions on the micrometric order are less than 500 μm and, preferably, less than 100 μm.

Microparticles exist that are provided with:
 at least one oblong flexible tail able to propel the microparticle in a solution along a trajectory thanks to beats transverse to the trajectory, each tail being provided for this purpose with at least one magnetic element causing beats of the tail under the action of an external alternating magnetic field non-collinear with the trajectory, and
 a head mechanically connected to a proximal end of the tail to limit the range of movement of the proximal end of the tail with relation to the range of movement of a distal end of the tail.

The solution is any medium in which tail beats enable the microparticle to advance along a trajectory. For example, the solution is a liquid presenting a more or less high viscosity such as water, glycerin, a solvent, etc. It may also be a soft medium such as gelatin. The solution may be a biological medium such as spinal marrow or albumin.

The magnetic force resulting in movement of these microparticles may enable the microparticles to be guided during their displacement, to concentrate them in certain locations, to deform them or magnetically excite them so that they dissipate energy and become heated.

By utilizing magnetic microparticles alone or by grafting different types of molecules onto their surface, enabling recognition of certain molecular or cellular species and/or an action on these species, numerous applications are possible. Among these applications may be cited the targeted delivery of treatment molecules (drug delivery), the sorting of molecules or cells in suspension (called MACS or Magnetic Cell Sorting), cancer treatments by hyperthermia, cell tissue engineering or use as contrast media in MRI (Magnetic Resonance Imaging).

For example, such microparticles are described in the following article D1:
Remi Dreyfus, Jean Baudry, Marcus R. Roper, Marc Fermigier, Howard A. Stone and Jérôme Bibette, "*Microscopic artificial swimmers*," Nature, Volume 437 of 6 Oct. 2005, page 862.

In article D1, the tail is magnetic, i.e., the tail bears at least one magnetic element displaced by the alternating magnetic field to cause tail beats. In article D1, the tail is made by the assembly of superparamagnetic microbeads. Thus, the cross section of this tail is necessarily circular. According to D1, an object of interest such as a red blood cell is added to the tail.

In addition, certain parameters, such as the displacement speed, of the microparticle strongly depend on the conformation of the tail. The utilization of an assembly of superparamagnetic microbeads considerably limits the shape variety of the microparticle.

Other particles having a non-magnetic tail have been described, for example, in the following articles:
S. Sudo, S. Segawa and T. Honda, "*Magnetic swimming mechanism in a viscous liquid*," Journal of Intelligent material systems and structures, volume 17-August/September 2006, page 729, Edition SAGE publications;
B. J. Nelson, "*Towards nanorobots*," Solid-state sensors, actuators and Microsystems conference, 2009, Transducers 2009, International IEEE, Piscataway, N.J., USA, 21 Jun. 2009 (2009-06-21), page 2155-2159, XP031545544 ISBN.

In the latter case, the method of propulsion of the particle is obtained by causing the tail to turn on itself like a propeller or screwing apparatus. The magnetic force enabling this rotation is only applied to the head, the tail being non-magnetic. The head turns under the effect of a revolving field resulting in the rotation of the tail that propels the assembly.

Such propulsion by full rotation of the head presents numerous disadvantages for the biomedical applications referred to above, the particle being entirely in rotation on itself thus resulting also in the rotation of the object of biological interest on itself In this context, the invention sets out to propose a magnetic microparticle that is easy to manufacture and capable of presenting a large variety of shapes and is particularly suitable for biomedical applications.

For this purpose, the invention proposes a microparticle comprising:
 at least one oblong flexible tail able to propel said microparticle in a solution along a trajectory thanks to beats transverse to the trajectory, said tail comprising for this purpose at least one magnetic element such that said magnetic element causes beats of said tail under the action of an external alternating magnetic field non-collinear with the trajectory,
 a head mechanically connected to a proximal end of the tail,
said microparticle being characterized in that the microparticle comprises at least one layer of a material formed from one piece and comprising said tail and said head,
the dimensions and/or shape of said head being chosen such that the beats of said proximal end of said tail are limited with respect to the beats of the distal end of the tail such that said head does not make a complete revolution around an axis parallel to the trajectory under the effect of said external alternating magnetic field.

It should be emphasized that a single alternating field in a same plane non-collinear to the position of the tail is sufficient to displace the microparticle according to the invention, unlike other microparticles or nanoparticles that require a revolving field or the superposition of two orthogonal planar fields so as to reconstitute a revolving field. This leaves the possibility for the invention to utilize for other purposes another possible planar magnetic field orthogonal to that which ensures the propulsion.

When the deposited magnetic layer (forming for example the layer from one piece) or magnetic layers is or are in a soft material, the magnetization of this magnetic layer or layers is spontaneously oriented along the largest dimension of the object to minimize the shape anisotropy energy. More precisely, shape anisotropy promotes an orientation of the magnetization of the tail along the length of the tail. This enables a torque to be exerted on the tail by using an external magnetic field applied transversely to the tail. On the other hand, the head, from its round, square or other less oblong shape, does not produce shape anisotropy, and very little when its shape differs a little from a circle; So its magnetization tends to be aligned with the alternating magnetic field by following it, and thus it undergoes almost no torque, so it does not move under the action of the field applied. Thus only the tail propels the assembly.

Thanks to the invention, the microparticle is displaced along the trajectory thanks to the transverse beats of the tail. Transverse beats correspond to displacements of the end of the tail that propel the microparticle along the trajectory in one direction or in the other while maintaining the head stable. According to the invention, it is the magnetic element of the tail that contributes to the displacement of the microparticle and not the head, which may or may not be magnetic. The head is considered to be stable when it does not make a complete revolution on itself around an axis parallel to the trajectory. For example, tail beats are undulations such that the tail functions like a flagellum. The propulsion method obtained is therefore totally different from that which would be obtained by causing the tail to turn on itself like a propeller.

The microparticle according to the invention is propelled by using an alternating magnetic field on an axis (and not necessarily a revolving field).

The fact of utilizing a layer forming the tail and the head from one piece enables different particle shapes to be made, in particular by utilizing photolithography or nanoimprint techniques. This layer from one piece ensures easy mechanical attachment of the tail to the head.

It will be noted that the material of the layer ensuring continuity between the head and the tail may or may not be magnetic; if the layer is not magnetic, depositing at least one magnetic portion on the tail so as to form the magnetic element should be understood.

Thus, the microparticle according to the invention may be formed:
  either from a single magnetic layer that forms the head and the tail (whose shape in top view is freely designed, for example by photolithography or nanoimprint);
  or from a non-magnetic layer, still from one piece, for example of copper, with magnetic portions deposited on at least one part of the tail.

The mechanical force that produces the beating or undulation of the tail is applied by the external alternating field directly on the magnetic parts of the tail.

It will be noted that the fact that the tail is provided with the magnetic element enables a more precise control of tail beats and, above all, a higher variety of beats than in the case where the magnetic elements are only provided in the head of the microparticle.

The microparticle according to the invention may also present one or more of the characteristics below, considered individually or according to all technically possible combinations:
  the dimensions and/or shape of said tail are chosen such that the direction of the magnetic moment of the tail is maintained in the longitudinal axis of the tail;
  said layer formed of one piece is a layer in a magnetic material;
  the magnetic material is a soft magnetic material, the shape of said head being chosen without shape anisotropy, for example a substantially round shape, such that the magnetic moment of said head is spontaneously aligned with the direction of the alternating magnetic field;
  the transverse dimensions of said head are chosen to be sufficiently large such that the direction of magnetization of said soft magnetic material is aligned with the direction of the alternating magnetic field;
  said magnetic material is a hard magnetic material of magnetization parallel to the length of said tail;
  said magnetic material is a magnetic material of spontaneous magnetization oriented out of the plane of said tail;
  said material is a non-magnetic material, one magnetic portion being at least deposited on said tail;
  the length of said tail is at least five times, preferentially 10 or 100 times, longer than one of the transverse dimensions of said tail;
  a biocompatible material is deposited on said layer;
  the microparticle according to the invention comprises an element of interest grafted onto said head;
  the microparticle comprises a first tail mechanically connected to the head and a second tail that is symmetrical with the first tail with respect to a plane perpendicular to the plane of the layer and passing by the center of gravity of the head;
  the tail systematically forms a bend between its proximal and distal ends in the absence of the alternating magnetic field;
  the head and the tail are planar and the plane of the layer of the tail is oblique with relation to the plane of the head.

In addition, the embodiments of the microparticle present the following advantages:
  a tail comprising a layer in one piece of material is easier to produce,
  when the layer utilized to form the tail is a magnetic material, this enables the tail and the magnetic element to be produced at the same time,
  producing the head and the tail in the same layer of soft magnetic material and the choice of dimensions of the head and the tail to enable or not enable alignment of the magnetic moment along the direction of the alternating magnetic field enables a different torque to be exerted on the tail and on the head when the tail and the head are produced from the same magnetic material,
  the use of a first and of a second tail that are symmetrical with each other improves the efficiency of displacement of the microparticle along a rectilinear trajectory,
  the use of a bent tail enables tail beats to be obtained by folding and unfolding this bend,
  a tail whose layers are oblique with relation to those of the head enables the surface of the tail bearing upon the solution to propel the microparticle to increase, and
  a length of the tail at least five times longer at one of its transverse dimensions enables a tail whose stiffness is sufficiently low for beating to be obtained.

Another object of the present invention is a method of manufacturing a microparticle according to the invention characterized in that the method comprises:
  the deposition and/or structuring of at least one layer deposited on a substrate to form the tail and the head from one piece;
  the release of the tail and head from the substrate.

Producing the tail and the head of the microparticle from one piece by deposition and/or structuring (for example by etching, typically photolithoetching, or by nanoimprint) of a layer enables a high diversity of shapes to be easily obtained for the magnetic tail. Consequently, the hydrodynamism of the tail of the microparticle is more easily optimized. The bottom line is, this enables, for example, microparticles that displace more rapidly under operational conditions identical to those described in article D1 to be obtained.

The manufacturing method also enables a wide variety of choice for the magnetic material utilized (soft or hard magnetic material, with magnetization parallel or perpendicular to the plane of the layer, etc.) to obtain the desired tail movement.

According to a preferential embodiment, the method according to the invention is a method to collectively manufacture a plurality of microparticles according to the invention, characterized in that the method comprises the following steps:
  producing an array of mesas on a substrate, said mesas being made of a sacrificial material and the top of each mesa presenting the shape of the microparticle to be made, said layer of material being formed of one piece and comprising said tail and said head;
  elimination of said first sacrificial material such that said particles are released.

According to a first embodiment, the collective manufacturing method comprises the following steps:
  deposition on a substrate of a layer of said sacrificial material;
  structuring the layer of sacrificial material by formation of said mesas whose tops present the form of the microparticles that one wishes to manufacture;
  deposition of said microparticle manufacturing material, said manufacturing material covering the tops of said mesas;
  removal of said sacrificial material such that the particles formed by said manufacturing material are released.

According to a second embodiment, the collective manufacturing method comprises the following steps:
  deposition on a substrate of a layer of said sacrificial material;
  deposition of at least one layer of said material to manufacture said microparticles;
  structuring of said layers of sacrificial material and of manufacturing material by formation of said mesas whose tops present the form of the microparticles that one wishes to manufacture;
  removal of said sacrificial material such that the particles formed by said manufacturing material are released.

These embodiments of the manufacturing method also present the following advantage:
  producing the head of the microparticle by deposition and/or etching of the same layer as that utilized to form the tail, enabling the tail to be fixed simply to the head. In addition, this limits viscous friction since the tail and head are flat.

The invention will be better understood upon reading the following description, given only by way of non-limiting example and done by referring to the drawings in which.

In these figures, the same references are used to designate the same elements.

In the rest of this description, the characteristics and functions that are well known to the person skilled in the art are not described in detail.

Figure 1:
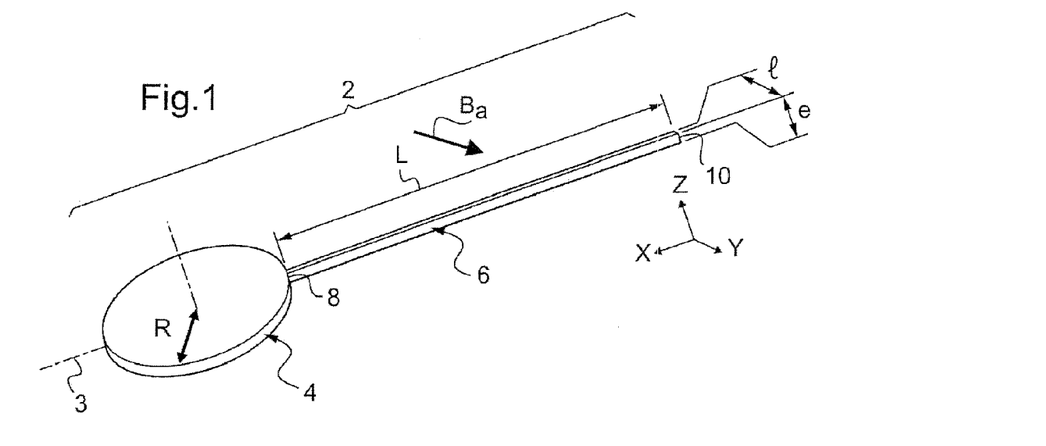
FIG. 1 is a schematic illustration in perspective of a microparticle according to the invention.

FIG. 1 represents a microparticle 2 able to be displaced along a trajectory 3 in a solution when an alternating magnetic field $B_a$ is applied in a direction non-collinear to trajectory 3. For example, the viscous liquid is water or glycerin or a solvent.

An example of a device enabling field $B_a$ to be applied on microparticle 2 is described in article D1 so that this device is not described here. In addition, this device also applies a continuous magnetic field whose direction is parallel to trajectory 3 to align and maintain microparticle 2 aligned with this trajectory.

Trajectory 3 here is a rectilinear trajectory. This trajectory is horizontal and extends parallel to a direction X. Field $B_a$ is substantially parallel to a horizontal direction Y perpendicular to direction X.

Microparticle 2 comprises a head 4 and a tail 6 produced from one piece in a same layer in a soft magnetic material.

Soft magnetic material is understood to refer to a magnetic material that, in absence of shape anisotropy, presents coercive field strength of less than 0.005 Tesla. In this description, a hard magnetic material is a material presenting coercive field strength of greater than 0.01 Tesla.

Tail 6 is oblong and flexible. The tail has a proximal end 8 that is mechanically fixed to head 4 and a free distal end 10.

The microparticle 2 is displaced along trajectory 3 thanks to transverse beats of tail 6. The transverse beats correspond to displacements of end 10 that propel microparticle 2 along trajectory 3 in one direction or in another while maintaining the head stable. The head is considered to be stable when it does not make a complete revolution on itself around an axis parallel to trajectory 3. For example, beats of tail 6 have undulations such that the tail operates as a flagellum. In the particular case described here, the beats correspond to a displacement of end 10 in a plane parallel to trajectory 3. Here the transverse beats are made in the X, Y plane. The beats of tail 6 imitate those of a flagellum to propel microparticle 2 in the solution. The propulsion method obtained is therefore totally different from that which would be obtained by causing the tail 6 to turn on itself like a propeller.

In FIG. 1, microparticle 2 is represented at rest, i.e., in the absence of field $B_a$. In this state, tail 6 extends along a longitudinal axis that coincides here with trajectory 3.

The dimensions of the tail 6 and the magnetic material are chosen to enable flexion of tail 6 under the effect of field $B_a$. Here, the stiffness of tail 6 is sufficiently low so that the tail curves in the XY plane in one or the other direction under the action of field $B_a$. Preferably, deformations of tail 6 caused by field $B_a$ are elastic deformations. For this purpose, the form factor of tail 6 is high, i.e., it is greater than five and, preferably, greater than 10 or 100. Form factor designates the ratio of length L of tail 6 measured between ends 8 and 10 over its mean dimension in a direction parallel to field $B_a$. Here, tail 6 is a parallelepiped. Its transverse dimensions, i.e., those perpendicular to its longitudinal axis 3, are thus constant over its entire length. Consequently, the form factor is the ratio of length L over width I of tail 6 in the Y direction. Here, the length L and width I are equal, respectively, to 50 μm and 0.35 μm. The thickness of the layer in magnetic material here is equal to 0.1 μm.

In addition, the transverse dimensions chosen of tail 6 are sufficiently small to maintain the easiest magnetization direction of the magnetic material parallel to axis 3 even when field $B_a$ is applied.

Head 4 is directly integrated with end 8 to limit the amplitude of movement of end 8 in comparison to the amplitude of movement of end 10 when field $B_a$ is applied. This dissymmetry between the amplitude of movements of ends 8 and 10 enables microparticle 2 to advance along trajectory 3 when field $B_a$ is applied.

For this purpose, the transverse dimensions of head 4 are larger than those of tail 6. This shape of head 4 enables the inertia of end 8 to be increased by increasing the viscous friction between head 4 and the solution. The continuous magnetic field applied on head 4 thus contributes to increasing the inertia of end 8 and to stabilizing head 4. This limits the amplitude of the movement of end 8 with relation to the amplitude of the movement of end 10 in the presence of the same field $B_a$.

In addition, the transverse dimensions of head 4 are chosen to be sufficiently large to enable the easiest magnetization direction of the soft magnetic material to be aligned with the direction of field $B_a$. For example, head 4 is a horizontal disc with a thickness e and a diameter of 5 μm. The flat shape of head 4 improves the hydrodynamism of microparticle 2.

Figure 2:
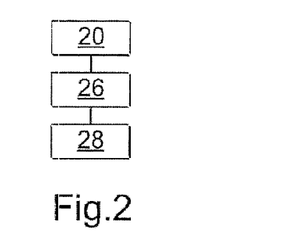
FIG. 2 is a flow chart of a method to manufacture the microparticle from FIG. 1, FIGS. 3 to 6 are schematic illustrations of various steps of the method from FIG. 2, FIGS. 7 and 8 are schematic illustrations of the operation of the microparticle from FIG. 1, FIGS. 9 to 11 are schematic illustrations in perspective of three other possible embodiments of a microparticle according to the invention.

A collective method to manufacture microparticles 2 will now be described with regard to the method of FIG. 2 and the illustrations of FIGS. 3 to 6.

Figure 3:
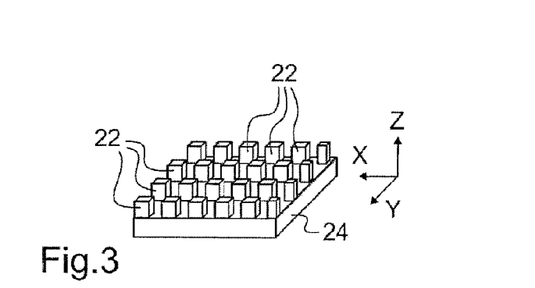

Initially, during step 20, an array of vertical mesas 22 is made on a substrate 24 (FIG. 3). These mesas 22 are made of a sacrificial material capable of being eliminated by using a solvent or another type of etching which is not going to destroy the microparticles 2.

The face at the top of each mesa 22 is identical to the horizontal section of microparticle 2. However, to simplify FIGS. 3, 5 and 6, this horizontal section is represented as being rectangular.

For example, the array of mesas 22 is made by optical or electronic lithography. It may also be made by nanoimprint. The sacrificial material used to make mesas 22 is a resist such as a polymer or any other material dissoluble in a solvent that does not destroy the microparticles 2.

Once mesas 22 are made, during step 26, one carries out the deposition of a layer of soft magnetic material on the tops of each mesas 22. For example, the layer of magnetic material is not deposited on the vertical faces of mesas 22.

Figures 4, 5, 6:
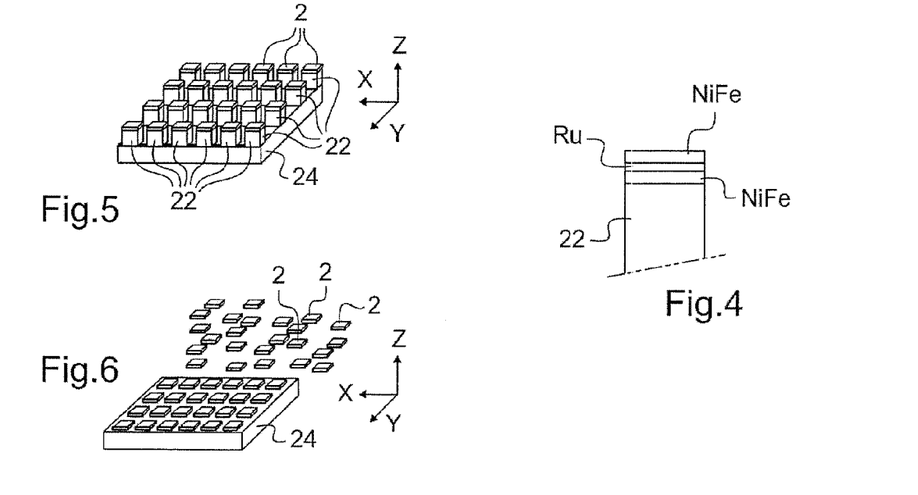

Here, the layer in soft magnetic material is made by a stack of three sub-layers, respectively in NiFe alloy, in ruthenium (Ru), and in NiFe alloy. The sub-layers are represented in FIG. 4. The result obtained after step 26 is represented in FIG. 5.

Then, during step 28, one carries out the release (or "lift off") of microparticles 2 of substrate 24. To do this, the sacrificial material is eliminated. For example, a solvent is used to release microparticles 2. Consequently, the microparticles 2 that were formed on the tops of mesas 22 get released in the solvent and become free to move in the solvent.

The result obtained after step 28 is represented in FIG. 6.

The method described here is a collective and simultaneous method to manufacture a multitude of microparticles 2. Additional information on such a manufacturing method may be found in the following document:

Wei Hu et al., "*High-moment antiferromagnetic nanoparticles tunable magnetic properties*," Advanced Materials, 2008, 20, 1479-1483, Willey-VCH, Verlag Gmbh and Co.

As will now be described in regard to FIGS. 7 and 8, a microparticle 2 thus manufactured is displaced in a viscous solution such as the solvent used during step 28 or any other viscous solution.

At time $t_1$ (FIG. 7) the direction of the magnetic field $B_a$ is contained in the XY plane and makes a non-zero angle θ with the Y direction.

Due to the transverse dimensions of tail 6, the magnetic moment $M_Q$ in tail 6 remains aligned with the longitudinal axis 3. In addition, here, the angle θ is chosen so as to systematically orientate the direction of the magnetic moment $M_Q$ of the tail towards the head. A high torque is thus exerted on tail 6 since the angular displacement between the directions of moment $M_Q$ and field $B_a$ is high.

At the same time, due to the larger transverse dimensions of head 4, the magnetic moment $M_t$ of head 4 is aligned with the direction of field $B_a$. The angular displacement between the directions of the magnetic moment $M_t$ and field $B_a$ is thus low. Consequently, the torque that is exerted on head 4 is at least twice less than that exerted on tail 6. Here, the torque on head 4 is zero or almost zero. Thus, in this embodiment, the particular geometry of microparticle 2 enables a higher torque to be exerted on tail 6 than on head 4 when the quantity of magnetic material in head 4 is higher or even much higher than the quantity of magnetic material in tail 6.

Figure 7:
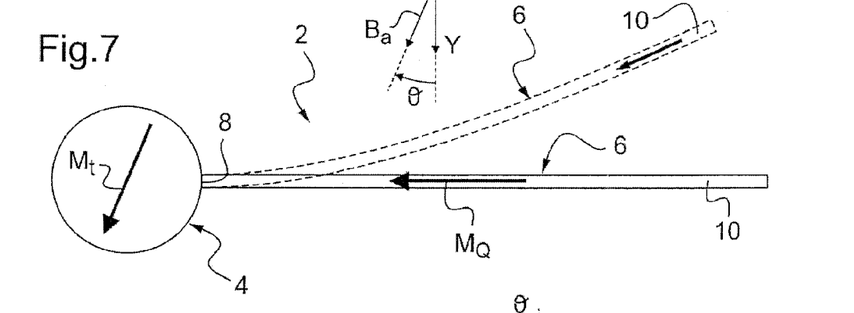

Under these conditions, tail 6 bends in the X, Y plane to reach a position such as that represented in dots in FIG. 7. Simultaneously, head 4 hardly turns at all.

At a later time $t_2$ (FIG. 8), field $B_a$ is symmetrical with respect to direction X of field $B_a$ at time $t_1$. As stated previously, the magnetic moment $M_Q$ of tail 6 remains aligned with the longitudinal axis of this tail while the magnetic moment $M_t$ of head 4 turns to be aligned with the direction of field $B_a$. Under these conditions, tail 6 bends in the X, Y plane to reach a position such as that represented by dots in FIG. 8.

Figure 8:
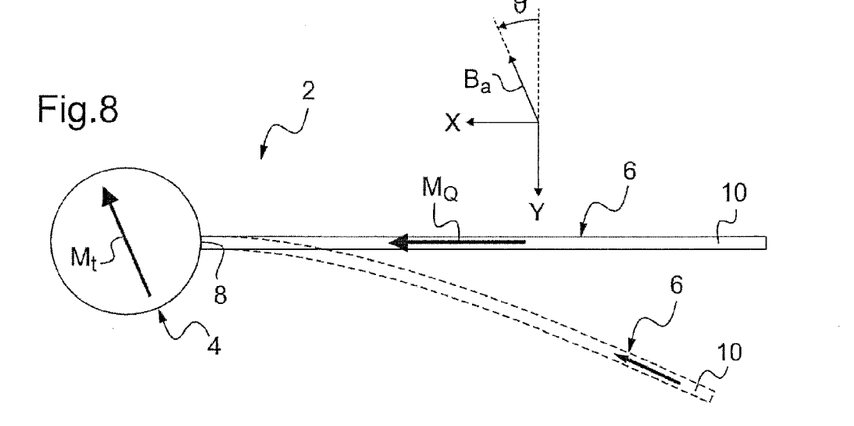

By alternating the direction of field $B_a$ between the two directions represented in FIGS. 7 and 8, a beat of tail 6 is obtained. This beat, like that of a flagellum, propels microparticle 2 along trajectory 3. During these beats, end 10 is displaced in the X, Y plane between the two extreme positions represented, respectively in FIGS. 7 and 8.

Figures 9, 10:
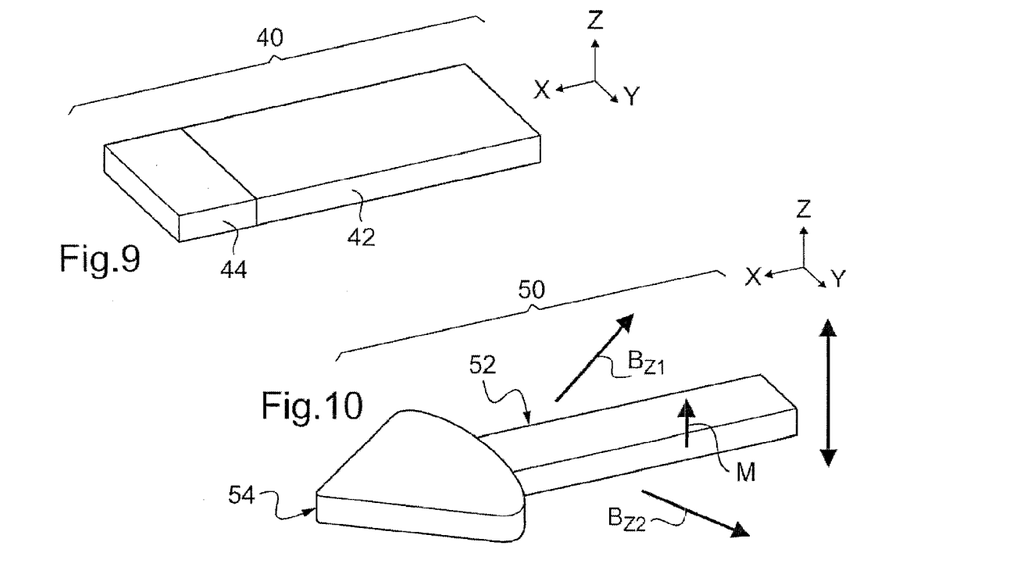

Many other embodiments of microparticle 2 are possible. For example, FIG. 9 represents a microparticle 40 comprising a tail 42 and a head 44. Tail 42 is, for example, identical to tail 6. Head 44 has a cross section identical to that of tail 42. However, head 44 is made of a material, for example a non-magnetic material, which is denser than the magnetic material used for tail 42. The inertia to displace the proximal end is thus higher than that to displace the distal end. Thus, this head 44 limits the amplitude of movement of the proximal end of tail 42 with respect to the amplitude of movement of its distal end without necessarily having a different cross section from that of tail 42.

FIG. 10 represents a microparticle 50 provided with a tail 52 and a pointed head 54. The direction of the magnetic moment M of tail 52 is parallel to direction Z, i.e., perpendicular to the plane of the layer of magnetic material used to make the tail 52. For this purpose, the magnetic material used to make tail 52 is a magnetic material presenting an anisotropy perpendicular to the plane of the layer. The magnetic material used is, for example, a multilayer composed of several layers of cobalt (Co) and platinum (Pt).

For example, head 54 is made of a soft magnetic material or a non-magnetic or amagnetic material.

This microparticle 50 is displaced in a solution when it is alternately subjected to two magnetic fields $B_{z1}$ and $B_{z2}$. Fields $B_{z1}$ and $B_{z2}$ are inclined with relation to the direction of moment M. Here, the directions of fields $B_{z1}$ and $B_{z2}$ are contained in a plane parallel to the X, Z plane and inclined, respectively, +45° and −45° with relation to the direction X.

The beat of tail 52 is then carried out in the vertical X, Z plane and not in the horizontal X, Y plane as described in regard to FIGS. 7 and 8. Under these conditions, the bearing surface of tail 52 on the solution is increased, which improves the efficiency of the displacement of the microparticle 50.

Figure 11:
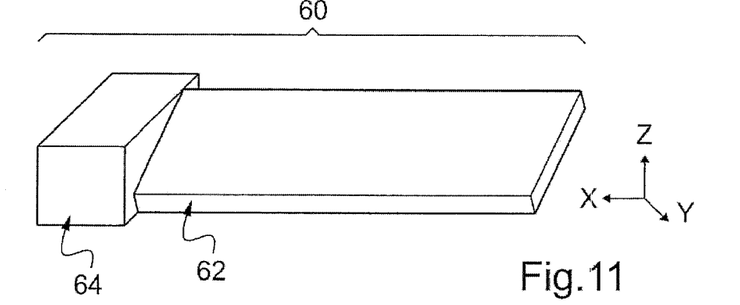

FIG. 11 represents a microparticle 60 provided with a tail 62 and a head 64. The head 64 is a parallelepiped whose largest faces are parallel to the X, Y plane.

Tail 62 is, for example, identical to tail 6 except for the fact that the plane of the layer that forms it is inclined with respect to the X, Y plane. This configuration of tail 62 enables the bearing surface of the tail on the solution to be increased and thus increases the propelling force. The bottom line is that this promotes the displacement of the microparticle 60.

Figure 12:
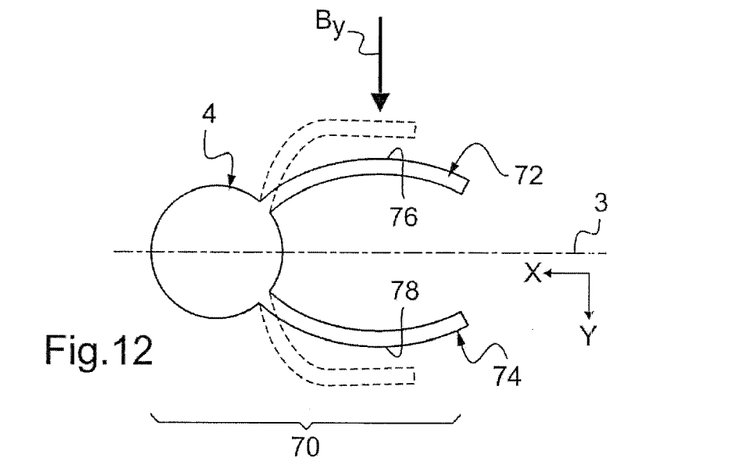
FIG. 12 is a schematic illustration in top view of another embodiment of the microparticle from FIG. 1, and FIGS. 13 and 14 are schematic illustrations in side view of other embodiments of the microparticle of FIG. 1.

FIG. 12 represents a microparticle 70 that is identical to microparticle 2 except for the fact that the tail 6 is replaced by two tails 72 and 74. Tails 72 and 74 are symmetrical with each other with respect to a vertical plane passing by the center of gravity of head 4. Here this vertical plane contains axis 3. At rest, each tail 72, 74 is curved so as to form a bend, respectively 76 and 78 in the X, Y plane. These bends are situated between the proximal and distal ends of the tail. For example, bends 76 and 78 are formed in the middle of the length of tails 72 and 74.

In FIG. 12, the position of tails 72 and 74 represented in thin lines corresponds to the position of these tails in the absence of an external alternating magnetic field. When an alternating magnetic field $B_y$ is applied parallel to direction Y, bends 76 and 78 fold such that tails 72 and 74 reach the positions represented in dotted lines in FIG. 12. When the magnetic field $B_y$ disappears again, the tails 72 and 74 find, for example by elastic deformation, their positions represented in solid lines. Thus, tails 72 and 74 perform a movement close to a breaststroke swimming movement to displace microparticle 70 in the presence of field $B_y$.

In this embodiment, tails 72 and 74 are made by using a soft magnetic material.

Figure 13:
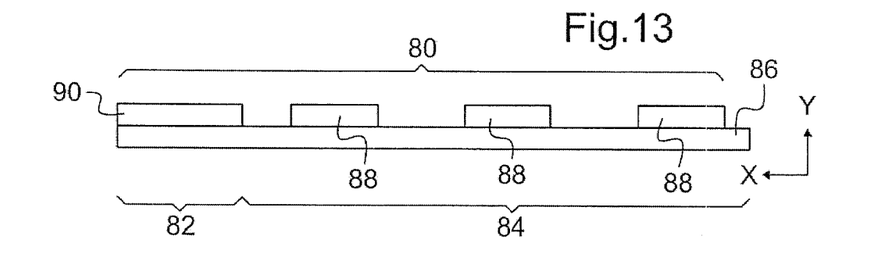

FIG. 13 represents in side view a microparticle 80 comprising a head 82 connected to a tail 84. Head 82 and tail 84 are made from a layer 86 in a non-magnetic material 86 from one piece.

Magnetic pads 88 are etched onto the surface 86 to form the magnetic elements of tail 84 that will allow it to beat in the presence of an external alternating magnetic field.

To increase the inertia of head 82, a pad 90 in a magnetic or non-magnetic material may be made on layer 86 at the level of the head 82.

Pads 88 and 90 are, for example, made by etching the same layer in a magnetic material during manufacturing of the microparticle 80.

FIG. 13 shows that the magnetic element with which the tail of the microparticle is provided is not necessarily a layer in magnetic material that extends continuously from the proximal end to the distal end. In addition, as represented, tail 84 may comprise several disjointed magnetic elements. However, in a variation, the tail comprises a single magnetic element such as a single pad 88.

Figure 14:
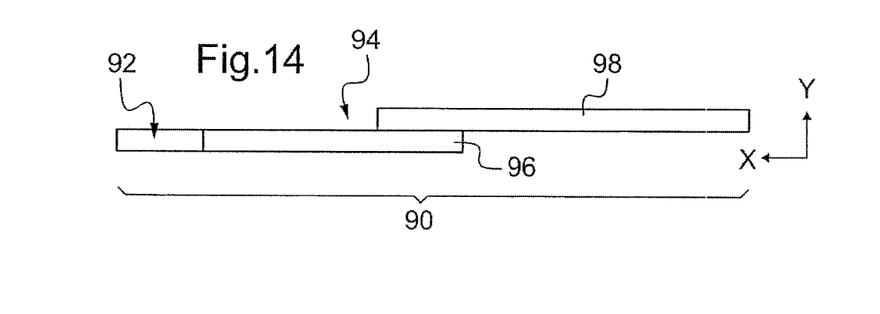

FIG. 14 represents, in side view, a microparticle 90 provided with a head 92 and a tail 94. Head 92 is made from a layer 96 of a magnetic or non-magnetic material.

The proximal end of tail 94 as well as a good part of tail 94 is also made in layer 96.

Tail 94 also comprises a layer 98, for example in a magnetic material, that extends beyond layer 96 parallel to direction X up to the distal end of tail 94. Layers 96 and 98 are overlapped one atop the other in an overlapping zone so as to mechanically connect the proximal and distal ends of tail 94.

Many different shapes are possible for the head of the microparticle, for example the head may be square, have the shape of a disc, a parallelepiped, or have an ellipsoidal, conical or other horizontal section. In general, the shape of the head is optimized in order to improve the hydrodynamism of the microparticle.

Tail beats are not necessarily limited to movements of the distal end in a plane. Depending on the shape of the tail and the direction of the alternating magnetic field applied, deformations of the tail may lead to displacements of the distal end outside of a plane.

The magnetic material utilized in the previous different embodiments may be soft or hard.

Thus, the particle is formed:
- either from a single magnetic layer that forms the head and the tail (whose shape in top view is freely designed, as any pattern obtained by photolithography or nanoimprint);
- Or from a non-magnetic layer, still from one piece (for example of copper), with magnetic portions deposited on top, in particular at the tail.

Preferably, when the head is made of a magnetic material, the head only forms one piece of material with the tail.

The cross section of the tail is not necessarily uniform. For example, the cross section may present bulges or may enlarge or, on the contrary, get narrower towards the distal end.

The microparticle may have two or more than three tails that are able to beat to propel the microparticle.

The tail of the microparticle is not necessarily rectilinear at rest. For example, in a particular embodiment, the proximal end of the tail is connected to the front of the head and then curves again to extend towards the back of the head.

Possibly, other layers than magnetic layers may also be deposited during step 26 of the manufacturing method. For example, external layers of the microparticle 2 are made of a biocompatible material such as gold or silica.

Other manufacturing methods than that in which mesas are made in a sacrificial material are usable. For example, the different layers that compose the microparticle may be deposited on a sacrificial layer, itself deposited on a substrate. Then, the stack of layers is etched to form the head and tail of the microparticle and then the sacrificial layer is eliminated to release the microparticle from the substrate. Several etching steps may be used so as to differently shape several of the layers from the stack of layers forming the microparticle. For example, several etching steps are necessary to produce the microparticle from the embodiments of FIGS. 13 and 14.

To displace the microparticle, an alternating field is necessary. However, it is not necessary that this alternating field changes sign.

In addition, it is no longer necessary that a continuous magnetic field be used to align the particles in the displacement direction. In fact, in order to displace the microparticle, it is sufficient to apply the alternating magnetic field in a direction not parallel to the magnetic moment of the magnetic elements in the tail. As soon as a slight misalignment exists between the direction of the magnetic field applied and the magnetic moment of the magnetic elements of the tail, the microparticle is likely to be displaced. However, ideally, the magnetic moment of the magnetic elements of the tail is perpendicular to the alternating magnetic field so as to maximize the efficiency of displacement.

Although it is not necessary, the alternating magnetic field may possibly be a rotating magnetic field, i.e., a field in which the direction rotates around an axis such as an axis collinear with trajectory 3; but this rotating magnetic field is not absolutely essential to the implementation of the invention.

Other propulsion actions may be added to the tail beat actions. For example, a magnetic field strength gradient may also be used or the microparticle may be carried by the flow of fluid.

Lastly, it will be noted that the alternating magnetic field is not necessarily sinusoidal or periodic. In particular, the speed of variation of the field may be different when the field tends to move the tail from its position at rest and when it tends to bring it back to its position at rest. For example, the field may be applied by successive pulses. During a first pulse, the magnetic field is only applied in one direction and then switched-off. After a time interval that is longer than the pulse time, a second magnetic field pulse is applied. During the second pulse, the magnetic field is for example applied in the opposite direction. These first and second pulses are alternately repeated to cause the microparticle to advance intermittently. For example, during the time interval when no magnetic field pulse exists, the tail relaxes to go back to its rest position. In this embodiment, the tail only undergoes elastic deformations.

The invention claimed is:

1. A microparticle comprising:
   at least one oblong flexible tail configured to propel said microparticle in a solution along a trajectory using beats transverse to the trajectory, said tail comprising at least one magnetic element such that said magnetic element causes said beats of said tail under the action of an external alternating magnetic field non-collinear with the trajectory,
   a head mechanically connected to a proximal end of the tail,
   wherein said microparticle comprises at least one layer of material formed from one piece and comprising said tail and said head, the dimensions and/or shape of said head being selected such that the beats of said proximal end of said tail are limited with respect to the beats of the distal end of the tail such that said head does not make a complete revolution around an axis parallel to the trajectory under the effect of said external alternating magnetic field.

2. The microparticle according to claim 1, wherein the dimensions and/or shape of said tail are selected such that the direction of the magnetic moment of the tail is maintained in a longitudinal axis of the tail.

3. The microparticle according to claim 1, wherein said layer formed from one piece is a layer of magnetic material.

4. The microparticle according to claim 3, wherein the magnetic material is a soft magnetic material, the shape of said head being selected without shape anisotropy such that the magnetic moment of said head is spontaneously aligned along the direction of the alternating magnetic field.

5. The microparticle according to claim 4, wherein the transverse dimensions of said head are selected to be sufficiently large such that a direction of magnetization of said soft magnetic material is aligned along the direction of the alternating magnetic field.

6. The microparticle according to claim 4, wherein the shape of said head is a substantially round shape.

7. The microparticle according to claim 1, wherein said magnetic material is a hard magnetic material of magnetization parallel to a length of said tail.

8. The microparticle according to claim 1, wherein said magnetic material is a magnetic material with spontaneous magnetization oriented out of the plane of said tail.

9. The microparticle according to claim 1, wherein said material is a non-magnetic material, a magnetic portion being at least deposited on said tail.

10. The microparticle according to claim 1, wherein a length of said tail is at least five times longer than one of the transverse dimensions of said tail.

11. The microparticle according to claim 10, wherein the length of said tail is at least from 10 to 100 times longer than one of the transverse dimensions of said tail.

12. The microparticle according to claim 1, wherein a biocompatible material is deposited on said layer.

13. The microparticle according to claim 1, wherein the microparticle comprises an element of interest grafted onto said head.

14. The microparticle according to claim 1, wherein the microparticle comprises a first tail mechanically connected to the head and a second tail that is symmetrical with the first tail with respect to a plane perpendicular to the plane of the layer and passing by a center of gravity of the head.

15. The microparticle according to claim 1, wherein the tail systematically forms a bend between proximal and distal ends thereof in the absence of the alternating magnetic field.

16. The microparticle according to claim 1, wherein the head and the tail are planar and the plane of the layer of the tail is oblique with respect to the plane of the head.

17. The microparticle according to claim 1, wherein the head includes a first end and a second end that is opposite the first end, wherein the first end is mechanically connected to the proximal end of the tail and wherein said at least one layer of material extends from said distal end of the tail to the second end of the head.

* * * * *

UNITED STATES PATENT AND TRADEMARK OFFICE
CERTIFICATE OF CORRECTION

PATENT NO. : 8,686,818 B2  
APPLICATION NO. : 13/060662  
DATED : April 1, 2014  
INVENTOR(S) : Bernard Dieny et al.

Page 1 of 1

It is certified that error appears in the above-identified patent and that said Letters Patent is hereby corrected as shown below:

On title page, item (75) Inventors
replace "Heélène Joisten, Granoble (FR)"
with -- Hélène Joisten, Grenoble (FR) --.

Signed and Sealed this
Twenty-fourth Day of June, 2014

Michelle K. Lee
*Deputy Director of the United States Patent and Trademark Office*